US010383956B2

(12) United States Patent
Urano et al.

(10) Patent No.: US 10,383,956 B2
(45) Date of Patent: Aug. 20, 2019

(54) FLUORESCENT PROBE FOR DETECTING DIPEPTIDYL PEPTIDASE IV

(71) Applicant: The University of Tokyo, Bunkyo-ku, Tokyo (JP)

(72) Inventors: Yasuteru Urano, Tokyo (JP); Yasuyuki Seto, Tokyo (JP); Haruna Onoyama, Tokyo (JP); Yugo Kuriki, Tokyo (JP); Mako Kamiya, Tokyo (JP)

(73) Assignee: The University of Tokyo, Tokyo (JP)

( * ) Notice: Subject to any disclaimer, the term of this patent is extended or adjusted under 35 U.S.C. 154(b) by 4 days.

(21) Appl. No.: 15/324,147

(22) PCT Filed: Jul. 10, 2015

(86) PCT No.: PCT/JP2015/069867
§ 371 (c)(1),
(2) Date: Jan. 5, 2017

(87) PCT Pub. No.: WO2016/006678
PCT Pub. Date: Jan. 14, 2016

(65) Prior Publication Data
US 2017/0157272 A1 Jun. 8, 2017

(30) Foreign Application Priority Data
Jul. 11, 2014 (JP) ................. 2014-143105

(51) Int. Cl.
*A61K 49/00* (2006.01)
*C12M 1/00* (2006.01)
*A61B 1/04* (2006.01)

(52) U.S. Cl.
CPC .......... *A61K 49/0041* (2013.01); *A61B 1/043* (2013.01); *A61K 49/00* (2013.01); *C12M 1/00* (2013.01)

(58) Field of Classification Search
CPC .................................................. A61K 49/00
See application file for complete search history.

(56) References Cited

U.S. PATENT DOCUMENTS

| 4,557,862 A | 12/1985 | Mangel |
| 4,640,893 A | 2/1987 | Mangel |
| 2002/0150885 A1 | 10/2002 | Weber et al. |
| 2006/0020141 A1 | 1/2006 | Banning |
| 2012/0021929 A1* | 1/2012 | Swiatek-de Lange ... C12Q 1/37 506/7 |

FOREIGN PATENT DOCUMENTS

| JP | 2001-104489 A | 4/2001 |
| JP | 2001519368 | 10/2001 |
| JP | 2004301681 | 10/2004 |
| JP | 2012526267 | 10/2012 |
| WO | 03/099780 | 12/2003 |
| WO | 2016137004 | 9/2016 |

OTHER PUBLICATIONS

Masayo Sakabe et al. (Rational Design of Highly Sensitive Fluroescence Probes for Protease and Glycosidase Based on Precisely COntrolled Spirocyclization, J. Am. Chem. Soc., 135, 409-414. (Year: 2013).*
Susan Lorey et al., Transcellular Proteolysis Demonstrated by Novel Cell Surface-associated Substrates of Dipeptidyl Peptidase IV (CD206), The J. Biol. Chem., 277(36), 33170-33177. (Year: 2002).*
International Search Report and Written Opinion dated Aug. 4, 2015 corresponding to International Patent Application No. PCT/JP2015/069867; 2 pages.
Mariusz Adam Goscinski, et al., "Dipeptidyl peptidase IV expression in cancer . . . ", APMIS 116, 2008, pp. 823-831.
Masayo Sakabe et al, "Rational Design of Highly Sensitive Fluorescence Probes for Protease and Glycosidase Based on Precisely Controlled Spirocyclization" Journal of The American Chemical Society, vol. 135, No. 1, Jan. 9, 2013 (Jan. 9, 2013) pp. 409-414.
Gossner et al., Comparison of methylene blue-directed biopsies and four-quadrant biopsies in the detection of high-grade intraepithelial neoplasia and early cancer in Barrett's oesophagus, Digestive and Liver DIS, W.B. Saunders, GB, vol. 38, No. 10, Oct. 1, 2006 (Oct. 1, 2006) pp. 724-729.
Lorey S. et al.,"New Fluorogenic Dipeptidyl Peptidase IV/CD26 Substrates and Inhibitors", Advances in Experimental Medicine and Biology; [Advances in Experimental Medicine and Biology], Springer, US, vol. 421, Jan. 1, 1997 (Jan. 1, 1997) pp. 157-160.
Lorey S. et al., "Transcellular proteolysis 1-15 demonstrated by novel cell surface-associated substrates of dipeptidyl peptidase IV (CD26)" Journal of Biological Chemistry, American Society for Biochemistry and Molecular Biology, vol. 277, No. 36, Sep. 6, 2002 (Sep. 6, 2002), pp. 33170-33177.
Mariusz Adam Goscinski et al: "Dipeptidyl peptidase IV expression in cancer and stromal cells of human esophageal squamous cell carcinomas, adenocarcinomas and squamous cell carcinoma cell lines", Apmis, Sep. 1, 2008 (Sep. 1, 2008 ), pp. 823-831.
Tomohiko Fujii et al: "In Vivo Imaging of Intraperitoneally Disseminated Tumors in Model Mice by Using Activatable Fluorescent Small-Molecular Probes for Activity of Cathepsins", Bioconjugate Chemistry, vol. 25, No. 10, Sep. 19, 2014 (2014), pp. 1838-1846.

(Continued)

*Primary Examiner* — Michael G. Hartley
*Assistant Examiner* — Jagadishwar R Samala
(74) *Attorney, Agent, or Firm* — Leason Ellis LLP

(57) ABSTRACT

[Problem] To provide a novel fluorescent probe for dipeptidyl peptidase IV, and a detection method and a detection kit using the fluorescent probe.
[Solution] A fluorescent probe for detecting dipeptidyl peptidase IV (DPP-IV), said probe comprising a compound represented by formula (I) or a salt thereof. In formula (I): A and B are either the same or different and independently represent an amino acid residue, provided that A is bonded via an amide bond to NH in an adjacent formula and B is bonded via an amide bond to A; $R^1$ represents hydrogen atom(s) or 1 to 4 substituents bonded to the benzene ring, said substituents being either the same or different; $R^2$, $R^3$, $R^4$, $R^5$, $R^6$ and $R^7$ independently represent a hydrogen atom, a hydroxyl group, an alkyl group or a halogen atom; $R^8$ and $R^9$ independently represent a hydrogen atom or an alkyl group; and X represents a $C_1$-$C_3$ alkylene group.

12 Claims, 8 Drawing Sheets

(56) References Cited

OTHER PUBLICATIONS

Haruna Onoyama et al: "Rapid and sensitive detection of early esophageal squamous cell carcinoma with fluorescence probe targeting dipeptidylpeptidase IV", Scientific Reports, vol. 6, No. 1, Jun. 1, 2016 (Jun. 1, 2016).
Database WPI Week 201665 Thomson Scientific, London, GB; AN 2016-53542PUNVI Tokyo: "New hydroxymethyl rhodamine green derivative used in agent for diagnosing or treating retinal diseases e.g. glaucoma, retinitis pigmentosa, age-related macular degeneration and retinal vascular occlusive disease."
Supplementary European Search Report dated Dec. 11, 2017 corresponding to European Patent Application No. EP15819326; 16 pages.
Office Action dated Jul. 2, 2019 in Japanese Patent Application No. 2016-532980.

* cited by examiner

HPLC chromatogram of GP-HMRG after reaction with DPPIV. Chromatograms of unreacted dye (7.1 min) and HMRG (8.9 min) are also shown. Elution was done with a linear gradient (eluent, 0 min, 20% CH$_3$CN/0.1% TFA aq. ~ 15 min, 80% CH$_3$CN/0.1% TFA aq., flow rate = 1.0 mL/min).

Fluorescence increase rate ( Ex / Em = 501 nm / 524 nm ) at 6 min of 1.1 μM probe in 20 mM Tris-HCl 18 μL and DPPIV solution in 20 mM Tris-HCl 2 μL. Incubated at 37 °C. Error bar represents S.D. (n = 4).

Normalized fluorescence intensity ( Ex / Em = 501 nm / 524 nm ) of 1.1 μM probe in 20 mM Tris-HCl 18 μL and DPPIV solution in 20 mM Tris-HCl 2 μL. Incubated at 37 °C. (n = 4).

FIG. 6 Maestro images of human esophageal cancer biopsy specimens (example using GP-HMRG)
The left side of the photographs are specimens from tumor areas and the right side are from non-tumor areas (the left side is listed as SCC and the right as no malignant findings in the histopathology diagnoses)

FIG. 7 Changes in fluorescence intensity by imaging of human esophageal cancer biopsy specimens
(solid lines are values of tumor areas, dotted lines those of non-tumor areas)

Maestro images of human esophageal cancer surgical specimens (example using GP-HMRG)

FIG. 8B    Comparison of images shown in Figure 8A with normal images and iodine-stained images Maestro images of human esophageal cancer ESD specimens (example using EP-HMRG)

FIG. 9B    Comparison of images shown in Figure 9(a) with normal images and iodine-stained images Maestro images of human esophageal cancer surgical specimens with inhibitor added

FLUORESCENT PROBE FOR DETECTING DIPEPTIDYL PEPTIDASE IV

TECHNICAL FIELD

The present invention relates to a fluorescent probe for detecting dipeptidyl peptidase IV. More specifically, it relates to a fluorescent probe for detecting the dipeptidyl peptidase IV expressed in cancer cells, a detection method using the fluorescent probe, and a detection kit comprising the probe.

BACKGROUND ART

Esophageal cancer affects many patients worldwide. The percentage of males afflicted in particular has been increasing year by year. The prognosis for esophageal cancer is generally known to be very poor among the cancers of the gastrointestinal tract, including stomach and colon cancers. The treatment of esophageal cancer consists of a single treatment method or a combination of multiple treatment methods selected from among endoscopic treatment, surgery, radiation treatment, and chemotherapy, depending on the disease stage. Surgery, however, which is the most common treatment method is highly invasive and also carries a high risk of complications such as respiratory tract complications, recurrent nerve paralysis, and suture failure. Although the results of surgery have improved in recent years, the recurrence rate and mortality rate are still said to be high in comparison to other cancers of the gastrointestinal tract.

Early detection of esophageal cancer not only makes it possible to avoid highly invasive surgery and permits radical treatment by relatively less invasive endoscopic treatment and chemoradiation therapy, but can also be expected to improve the long-term prognosis thereafter. In addition, evaluation of the resection margin also becomes possible and residual-free treatment can be carried out if cancer tissue can be detected during surgery or endoscopic submucosal dissection (ESD). Given this background, the development of a method for detecting esophageal cancer quickly and accurately is strongly desired.

However, since early esophageal cancer is difficult to discover by ordinary endoscopic examination alone, iodine agents were often used in combination. The problem, however, was that they have strong symptoms of irritation such as heartburn and discomfort and cannot be used in patients with an iodine allergy.

On the other hand, dipeptidyl peptidase IV (DPP-IV), which is an enzyme that specifically removes a dipeptide from the N-end of proteins and polypeptides, is known to be related to many disease states. It was recently clarified that dipeptidyl peptidase IV is expressed at a higher level than in normal cells in esophageal cancer tissue (Non-Patent Reference 1).

PRIOR ART REFERENCES

Non-Patent References

Non-patent Reference 1: Goscinski et al., APMIS, 116, 823-31, 2008.

DISCLOSURE OF THE INVENTION

Problems to be Solved by the Invention

Therefore, the present invention focuses on the dipeptidyl peptidase IV that is expressed at a high level in esophageal cancer tissue and has as its purpose to provide a novel fluorescent probe for such peptidase with the goal of developing a means of detecting esophageal cancer quickly and at high sensitivity.

Means Used to Solve the Above-Mentioned Problems

As a result of in-depth studies intended to solve the above problems, the present inventors discovered that dipeptidyl peptidase IV can be detected specifically by an on/off fluorescence response by using a compound with a xanthene skeleton having a dipeptide site as a fluorescent probe and that this makes it possible to detect esophageal cancer quickly and at high sensitivity. The present invention was completed based on these findings.

Specifically, the present invention, in one embodiment, provides a fluorescent probe for detecting dipeptidyl peptidase IV (DPP-IV) comprising a compound represented by formula (I) below or a salt thereof.

[Chemical formula 1]

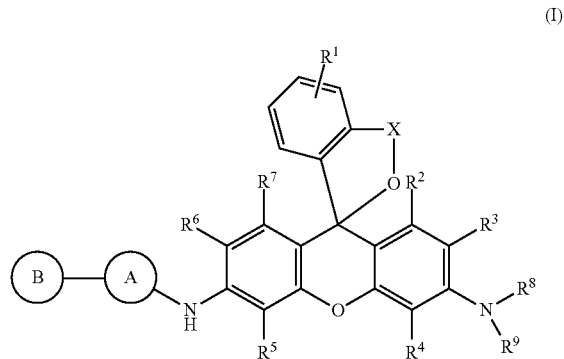

(I)

In the formula, A and B are either the same or different and independently represent amino acid residues; provided that A is bonded via an amide bond to NH in an adjacent formula and B is bonded via an amide bond to A; $R^1$ represents hydrogen atom or one to four of the same or different substituents bonded to a benzene ring; $R^2$, $R^3$, $R^4$, $R^5$, $R^6$, and $R^7$ each independently represent a hydrogen atom, hydroxyl group, alkyl group, or halogen atom; $R^8$ and $R^9$ each independently represent a hydrogen atom or alkyl group; X represents a $C_1$-$C_3$ alkylene group.

In the above formula (I), A is preferably an amino acid residue selected from proline or alanine. B is preferably an amino acid residue selected from glycine, glutamic acid, lysine, tyrosine, leucine, or proline. More preferably, A is a proline residue and B is a glycine residue.

Also in the above formula (I), $R^1$, $R^2$, $R^3$, $R^4$, $R^5$, $R^6$, $R^7$, $R^8$, and $R^9$ are preferably hydrogen atoms, and X is preferably a methylene group.

In a preferred embodiment of the present invention, the compound represented by formula (I) or salt thereof is a compound selected from the following group, or a salt thereof.

[Chemical formula 2]

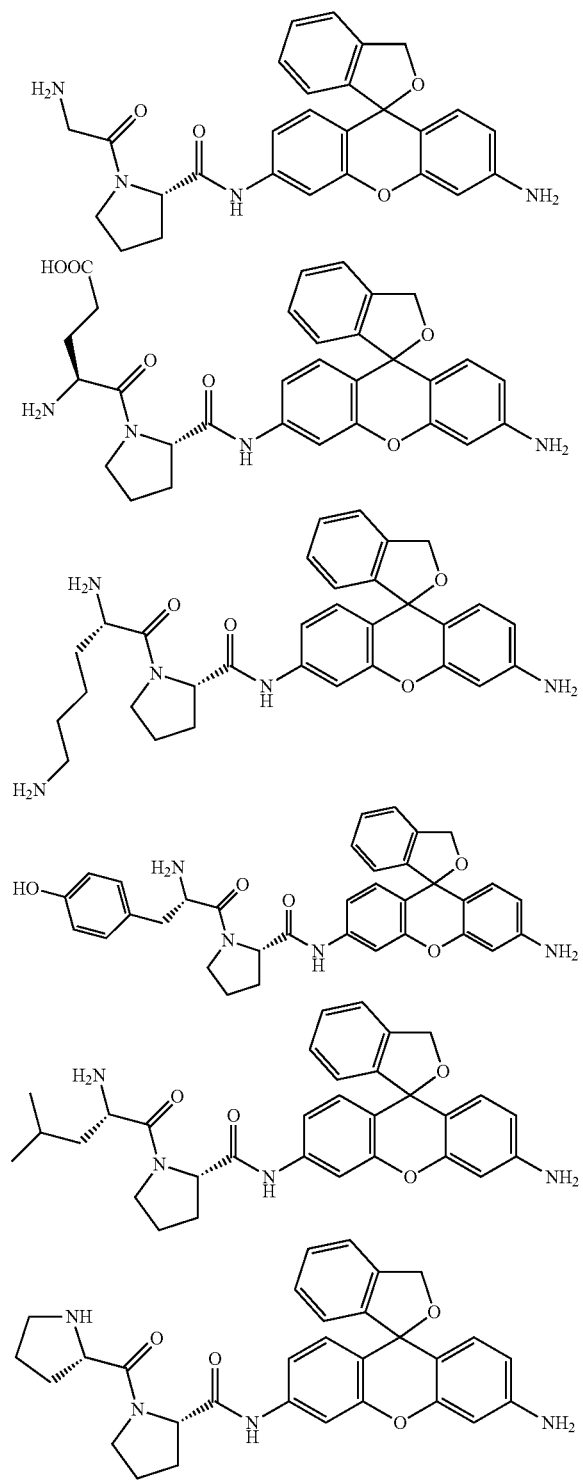

In another embodiment, the present invention provides a method for detecting dipeptidyl peptidase IV characterized by comprising a step for bringing a sample into contact with the above fluorescent probe outside the body and a step for observing the fluorescence response due to the reaction of the dipeptidyl peptidase IV (DPP-IV) contained in the sample and the fluorescent probe. Preferably, this method is further characterized by the fact that the fluorescence response is visualized using fluorescent imaging means.

In yet another embodiment, the present invention provides a method for detecting target cells that express dipeptidyl peptidase IV (DPP-IV) using the above fluorescent probe. Preferably, the target cells are cancer cells; more preferably, the cancer cells are esophageal cancer cells.

In yet another embodiment, the present invention provides a kit for detecting dipeptidyl peptidase IV (DPP-IV) comprising the above fluorescent probe.

In yet another embodiment, the present invention is a device for bringing a chemical solution containing the above fluorescent probe into contact with a sample to be measured wherein the device is equipped with a chemical solution housing unit for housing a chemical solution comprising the above fluorescent probe and a chemical solution spraying unit constructed to make it possible to spray the chemical solution onto the sample. Preferably, the device can also be equipped with fluorescent imaging means for observing the fluorescence response due to the reaction of the dipeptidyl peptidase IV (DPP-IV) contained in the sample and the above fluorescent probe. In a preferred embodiment, the above device can be an endoscope.

Advantages of the Invention

The present invention makes it possible to detect the dipeptidyl peptidase IV expressed at a high level in esophageal cancer tissue with a fluorescence response by using a compound with a xanthene skeleton having an amino acid residue as a fluorescent probe and thereby achieves the exceptional effect of making it possible to specify and image the presence of esophageal cancer accurately, quickly, and at high sensitivity.

The fluorescent probe of the present invention makes possible the early detection of esophageal cancer by being used, for example, during endoscopic examination, and makes possible radical treatment by less invasive endoscopic treatment and chemoradiation therapy without highly invasive surgical treatment. It also makes possible evaluation of the resection margin by adaptation during ESD or surgery, and can be expected to permit residual-free treatment. The problems of symptoms of irritation such as heartburn and discomfort to the patient as encountered when using conventional iodine agents and the inability to use them in patients with an iodine allergy are also solved. Therefore, the present invention can be said to have extremely high medical and industrial utilization value and economic value.

In addition, the detection method using the fluorescent probe of the present invention permits detection by visible light that is safe for the living body, in addition to the detection procedure being simple. The amount of fluorescent probe that needs to be used is also minuscule. The detection method using the fluorescent probe of the present invention also has excellent utility in this regard.

BEST MODE FOR CARRYING OUT THE INVENTION

Figure 1:
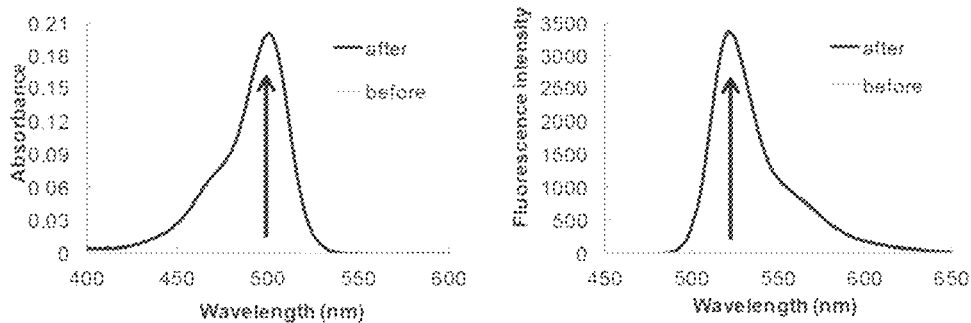
FIG. 1 Shows the changes in the absorption spectrum and changes in the fluorescence spectrum due to addition of DPP-IV to GP-HRMG, which is a fluorescent probe of the present invention.

Embodiments of the present invention are explained below. The scope of the present invention is not restricted to these explanations; the present invention can be implemented with suitable variations even outside the following examples as long the spirit of the invention is not impaired.

1. Definitions

In this specification, a "halogen atom" means a fluorine atom, chlorine atom, bromine atom, or iodine atom.

In this specification, "alkyl" may be any straight-chained, branched, cyclic, or combination thereof aliphatic hydrocarbon group. The number of carbon atoms of an alkyl group is not particularly restricted, but is, for example, 1-20 ($C_{1-20}$), 3-15 ($C_{3-15}$), or 5-10 ($C_{5-10}$). When the number of carbon atoms is specified, it means an "alkyl" having a number of carbon atoms within that numerical range. For example, $C_{1-8}$ alkyls include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl, and the like. In this specification an alkyl group may have one or more optional substituents. Examples of these substituents include, but are not limited to, an alkoxy group, halogen atom, amino group, mon- or di-substituted amino group, substituted silyl group, acyl, or the like. When an alkyl group has two or more substituents, they may be the same or different. The same is also true for the alkyl moiety of other substituents (for example, an alkoxy group, arylalkyl group, or the like) including an alkyl moiety.

In this specification, when certain functional groups are defined as "optionally substituted," the type of substituent, substitution position, and number of substituents are not particularly restricted. When there are two or more substituents, they may be the same or different. Examples of substituents include, but are not limited to, an alkyl group, alkoxy group, hydroxyl group, carboxyl group, halogen atom, sulfo group, amino group, alkoxycarbonyl group, oxo group, and the like. Other substituents may be present in these substituents. Examples of such cases include, but are not limited to, a halogenated alkyl group, dialkylamino group, and the like.

In this specification, an "alkoxy group" refers to a structure in which an alkyl group above is bonded to an oxygen atom; examples including saturated alkoxy groups which are linear, branched, cyclic, or a combination thereof. Preferred examples include a methoxy group, ethoxy group, n-propoxy group, isopropoxy group, cyclopropoxy group, n-butoxy group, isobutoxy group, s-butoxy group, t-butoxy group, cyclobutoxy group, cyclopropylmethoxy group, n-pentyloxy group, cyclopentyloxy group, cyclopropylethyloxy group, cyclobutylmethyloxy group, n-hexyloxy group, cyclohexyloxy group, cyclopropylpropyloxy group, cyclobutylethyloxy group, cyclopentylmethyloxy group, and the like.

In this specification, an "aryloxy group" is a group in which the aryl group bonds via an oxygen atom. Examples of aryloxy groups include a phenoxy group, 2-thienyloxy group, 3-thienyloxy group, 2-pyridyloxy group, 3-pyridyloxy group, 4-pyridyloxy group, 2-furyloxy group, 3-furyloxy group, 2-thiazolyloxy group, 4-thiazolyloxy group, 5-thiazolyloxy group, 2-oxazolyloxy group, 4-oxazolyloxy group, 5-oxazolyloxy group, 1-pyrazolyloxy group, 3-pyrazolyloxy group, 4-pyrazolyloxy group, 2-pyrazinyloxy group, 2-pyrimidinyloxy group, 4-pyrimidinyloxy group, 5-pyrimidinyloxy group, 1-pyrolyloxy group, 2-pyrolyloxy group, 3-pyrolyloxy group, 1-imidazolyloxy group, 2-imidazolyloxy group, 4-imidazolyloxy group, 3-pyridazinyloxy group, 4-pyridazinyloxy group, 3-isothiazolyloxy group, 3-isoxazolyloxy group, 1,2,4-oxadiazol-5-yloxy group, 1,2,4-oxadiazol-3-yloxy group, and the like.

In this specification, "alkylamine" and "arylamino" mean an amino group in which hydrogen atoms of an —$NH_2$ group have been substituted by one or two of the alkyls or aryls. Examples include methylamino, dimethylamino, ethylamino, diethylamino, ethylmethylamino, benzylamino, and the like. Similarly, "alkylthio" and "arylthio" mean a group in which hydrogen atoms of a —SH group have been substituted by the alkyl or aryl. Examples include methylthio, ethylthio, benzylthio, and the like.

"Amide" as used in this specification includes both RNR'CO— (when R=alkyl, alkylaminocarbonyl-) and RCONR'— (when R=alkyl, alkylcarbonylamino-).

In this specification, the phrase "ring structure" means a heterocyclic or carbocyclic group when formed by a combination of two substituents. Such groups may be saturated, unsaturated, or aromatic. Therefore, it includes the cycloalkyls, cycloalkenyls, aryls, and heteroaryls defined above. Examples include cycloalkyl, phenyl, naphthyl, morpholinyl, piperidinyl, imidazolyl, pyrrolidinyl, and pyridyl. In this specification, substituents can form ring structures with other substituents, and those skilled in the art can understand that a specific substitution, for example, bonding to hydrogen, is formed when such substituents bond to each other. Therefore, when it is stated that specific substituents together form a ring structure, those skilled in the art can understand that this ring structure can be formed by an ordinary chemical reaction or is generated easily. Any such ring structures and their formation processes are within the purview of those skilled in the art.

2. Fluorescent Probe Molecule

The fluorescent probe of the present invention is characterized by having a structure in which a dipeptide site that serves as a substrate of dipeptidyl peptidase IV has been introduced into a xanthene skeleton and, in one embodiment, includes a compound having a structure represented by the following formula (I).

[Chemical formula 3]

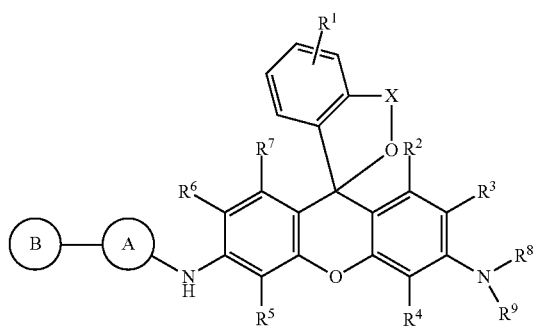

In general formula (I), $R^1$ represents a hydrogen atom or from one to four substituents bonded to a benzene ring. Examples of substituents include, but are not limited to, an alkyl group, alkoxy group, halogen atom, amino group, mono- or di-substituted amino group, substituted silyl group, acyl group, or the like. When there are two or more substituents on the benzene ring, they may be the same or different. $R^1$ is preferably a hydrogen atom.

$R^2$, $R^3$, $R^4$, $R^5$, $R^6$, and $R^7$ each independently represent a hydrogen atom, hydroxyl group, alkyl group, or halogen atom. $R^2$ and $R^7$ are preferably hydrogen atoms. $R^3$, $R^4$, $R^5$, and $R^6$ are also preferably hydrogen atoms. It is more preferred that $R^2$, $R^3$, $R^4$, $R^5$, $R^6$, and $R^7$ are all hydrogen atoms.

$R^8$ and $R^9$ each independently represent a hydrogen atom or alkyl group. When both $R^8$ and $R^9$ are alkyl groups, they may be the same or different. For example, it is preferred when $R^8$ and $R^9$ are both hydrogen atoms, and when $R^8$ is an alkyl group and $R^9$ is a hydrogen atom, and more preferred when both $R^8$ and $R^9$ are hydrogen atoms.

X represents a $C_1$-$C_3$ alkylene group. The alkylene group may be a linear alkylene group or a branched alkylene group. For example, in addition to a methylene group (—$CH_2$—), ethylene group (—$CH_2$—$CH_2$—), and propylene group (—$CH_2$—$CH_2$—$CH_2$—), —$CH(CH_3)$—, —$CH_2$—$CH(CH_3)$—, —$CH(CH_2$—$CH_3)$—, and the like can also be used as branched alkylene groups. Among them, a methylene group or ethylene group is preferred, and a methylene group is more preferred.

A and B each independently represent the same or different amino acid residues. Here, A bonds by forming an amide bond with the adjacent NH in the formula, that is, bonds with the xanthene skeleton by the carbonyl moiety of the amino acid residue A and the NH of formula (I) forming an amide bond. Furthermore, A can bond with B in the same way as an ordinary peptide chain. As a result, B bonds by forming an amide bond with A. In this specification, an "amino acid residue" means a structure corresponding to the partial structure remaining after a hydroxyl group has been removed from a carboxyl group of an amino acid. Therefore, B has a structure the same as a so-called N-end residue, and A, which is the middle amino acid residue, can bond with B in the same way as an ordinary peptide chain.

In this specification, an "amino acid" includes natural and unnatural compounds and an arbitrary compound can be used as long as it is a compound having both an amino group and a carboxyl group. Neutral amino acids, basic amino acids, and acidic amino acids are all acceptable, and amino acids that are structural components of bioactive peptides (including oligopeptides as well as dipeptides, tripeptides, and tetrapeptides), proteins, and other such polypeptide compounds can be used in addition to amino acids that themselves function as neurotransmitters and other such transmitters. Examples include α amino acids, β amino acids, γ amino acids, and the like, lit is preferable to use an optically active amino acid as an amino acid. For example, either the D- or L-amino acid of an a amino acid may be used, but it is sometimes preferable to select an optically active amino acid that functions in the living body.

From the viewpoint of the purpose of the present invention, which is to detect dipeptidyl peptidase IV, A and B are preferably a combination of amino acid residues that are substrate peptides of dipeptidyl peptidase IV (DPP-IV) and can be selectively hydrolyzed readily. More specifically, A is preferably an amino acid residue selected from proline or alanine, and B is preferably an amino acid residue, selected from glycine, glutamic acid, lysine, tyrosine, leucine, or proline. More preferably, A is a proline residue and B is a glycine residue.

Concrete examples of compounds of formula (I) include compounds of formulas 1-6 below. However, examples are not limited to these.

[Chemical formula 4]

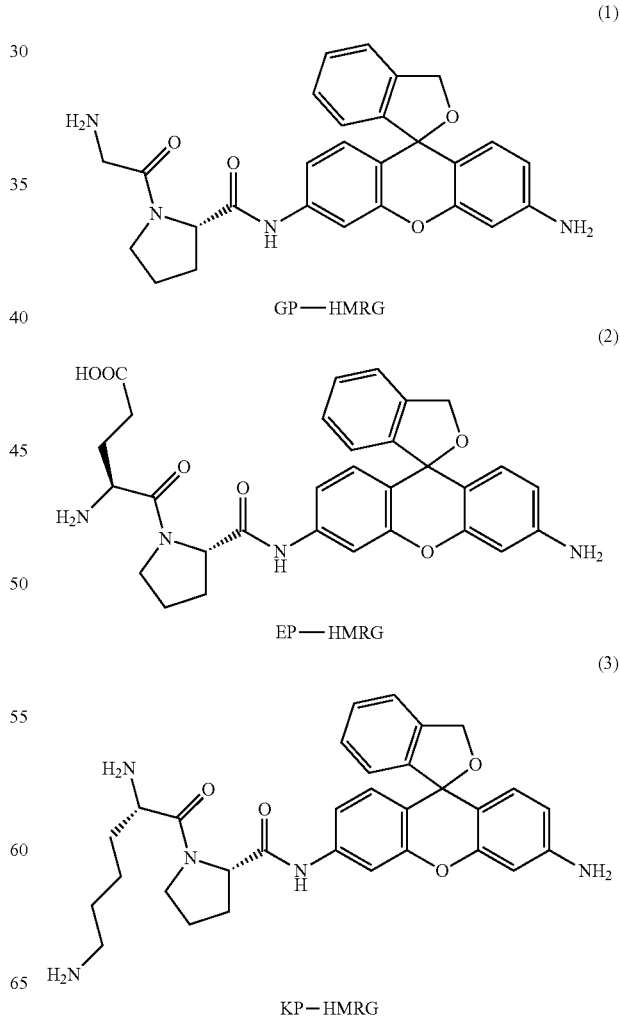

-continued (4)

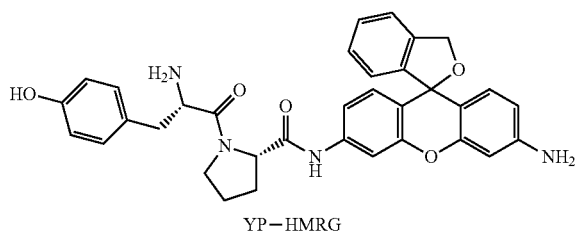

YP—HMRG (5)

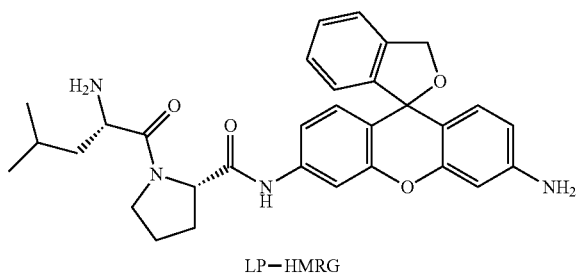

LP—HMRG (6)

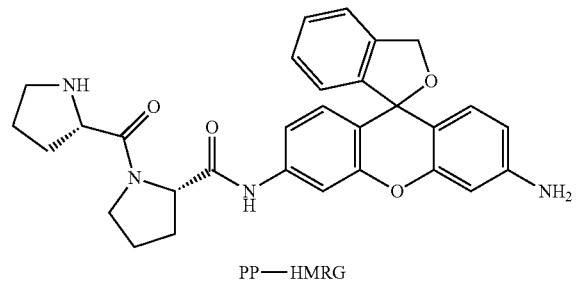

PP—HMRG

As is evident from these chemical structures, compounds of formulas 1-6 are examples in which the combination of A and B (A-B) is, in order, proline-glycine; proline-glutamic acid; proline-lysine; proline-tyrosine; proline-leucine; and proline-proline.

Compounds represented by the above general formula (I) may exist as salts. Examples of such salts include base addition salts, acid addition salts, amino acid salts, and the like. Examples of base addition salts include sodium salts, potassium salts, calcium salts, magnesium salts, and other such metal salts, ammonium salts, or triethylamine salts, piperidine salts, morpholine salts, or other such organic amine salts. Examples of acid addition salts include hydrochlorides, sulfates, nitrates, and other such mineral acid salts, carboxylases, methanesulfonates, p-toluenesulfonates, citrates, oxalates, and other such organic acid salts. Examples of amino acid salts include glycine salts and the like. However, salts are not limited to these.

Compounds represented by formula (I) may have one or more asymmetric carbons depending on the types of substituents, and sometimes exist as optical isomers, diastereomers, or other such stereoisomers. Stereoisomers of a pure form, any mixtures of stereoisomers, racemates, and the like are all encompassed within the scope of the present invention.

Compounds represented by formula (I) or salts thereof may also exist as hydrates or solvates. These substances are all encompassed within the scope of the present invention. The type of solvent for forming a solvate is not particularly restricted; examples include ethanol, acetone, isopropanol, and other such solvents.

Compounds represented by general formula (I) can be produced easily, for example, by acylating the position 3 amino group after having converted the position 9 2-carboxyphenyl group or 2-alkoxycarbonylphenyl group into a hydroxyalkyl group using as the raw material a xanthene compound having amino groups at positions 3 and 6 and having a 2-carboxyphenyl group or 2-alkoxycarbonylphenyl group at position 9. Examples of 3,6-diaminoxanthene compounds that can be used as the raw material include the commercially available rhodamine 110 and rhodamine 123. Compounds, however, are not limited to these, and suitable xanthene compounds can be selected in accordance with the structure of the target compound. In addition, a fluorescent probe having the same functions as general formula (I) in the present invention can also be produced by using a compound having a skeleton of a form in which oxygen atoms of the xanthene skeleton moiety in a compound represented by general formula (I) have been substituted by a C atom or Si atom having specific substituents or a Ge atom or Pb atom.

Additionally, since methods for producing representative compounds included among compounds of the present invention represented, by general formula (I) are illustrated concretely in the examples, of this specification, those skilled in the art can produce arbitrary compounds encompassed by general formula (I) easily by referring to the disclosure of this specification and suitably selecting the starting raw material and reagents, reaction conditions, and the like as needed.

The above fluorescent probe may be used as a composition by compounding with additives commonly used in the preparation of reagents as needed. For example, dissolution auxiliaries, pH adjusters, buffers, isotonifying agents, and other such additives can be used as additives for use in a physiological environment, and the amounts compounded can be selected as is appropriate by one skilled in the art. These compositions can be provided as a composition of a suitable form such as a mixture in powdered form, freeze-dried product, granules, tablets, or the like.

3. Light Emission Mechanism of the Fluorescent Probe Molecule

Compounds shown by the above formula (I) are the skeleton of the xanthene fluorescent dyes widely used in bioimaging due to their high water solubility, high fluorescence quantum yield, and the like, but the fluorescent probe itself is substantially non-absorbing/non-fluorescent (fluorescence response in an "off" state) in the neutral region (for example, a pH range of 5-9) when the upper portion of the xanthene skeleton is in a closed ring state. In contrast to this, the dipeptide site in B-A-NH is hydrolyzed by dipeptidyl peptidase IV, rapidly becoming a ring-opened tautomer when cleaved from the xanthene skeleton, and producing the following strongly fluorescent compound.

[Chemical formula 5]

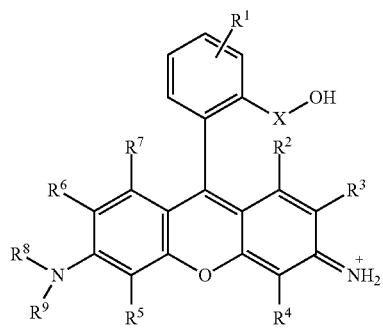

Specifically, the fluorescent probe of the present invention that includes as an active ingredient a compound represented by general formula (I) or a salt thereof has the property of being hydrolyzed by the dipeptidyl peptidase IV expressed in esophageal cancer tissue and giving the above ring-opened compound that emits strong fluorescence. Therefore, the use of the fluorescent probe of the present invention makes it possible to observe dipeptidyl peptidase IV by the change in fluorescence intensity and thereby to detect the presence of esophageal cancer expressing this dipeptidyl peptidase IV.

More specifically, for example, a compound represented by general formula (I) or a salt thereof emits virtually no fluorescence when irradiated by excitation light of, for example, about 440-510 nm, in the neutral region, but the above ring-opened compound emits very strong fluorescence (for example, emission: 524 nm) under the same conditions. Therefore, visible light of about 440-510 nm may usually be irradiated when conducting detection using the fluorescent probe of the present invention. The fluorescence wavelength to be observed is usually about 510-800 nm; it is preferable to observe, for example, fluorescence of about 516-556 nm.

A compound represented by the above formula (I) or a salt thereof may be used without modification as the fluorescent probe of the present invention, but may be used as needed as a composition by compounding additives commonly used in the preparation of reagents. For example, dissolution auxiliaries, pH adjusters, buffers, isotonifying agents, and other such additives can be used as additives for use in a physiological environment, and the amounts compounded can be selected as is appropriate by one skilled in the art. These compositions can be provided as a composition of a suitable form such as a mixture in powdered form, freeze-dried product, granules, tablets, liquid, or the like, but should be used by dissolution in distilled water for injection or a suitable buffer at the time of use.

Furthermore, the fluorescent probe of the present invention can be used, for example, during surgery, during testing, or after surgery. The term "surgery" in this specification encompasses any surgery, including endoscopy or laparoscope, and other such endoscopic surgery. In addition, the term "testing" encompasses testing conducted on tissue separated and removed from a living body, in addition to testing using an endoscope and tissue resection, collection, and other such treatments associated with testing. These terms must be interpreted in their broadest sense, and no meaning should be interpreted in a limited way.

4. Detection Method Using the Fluorescent Probe

In accordance with such a light emission mechanism, the method for detecting dipeptidyl peptidase IV of the present invention is characterized by comprising a step for bringing the above fluorescent probe into contact with a sample outside the body and a step for observing the fluorescence response due to the reaction of the dipeptidyl peptidase IV contained in the sample and the fluorescent probe. Detecting dipeptidyl peptidase IV by such a method also makes it possible to detect target cells that express dipeptidyl peptidase IV. The target cells are preferably cancer cells, more preferably esophageal cancer cells. The term "detection" in this specification should be interpreted in the broadest sense to include quantitative, qualitative, and other such measurements for various purposes.

A fluorometer having a wide measurement wavelength can be used as the means for observing the fluorescence response, but the fluorescence response can also be visualized using fluorescent imaging means that permits display as a two-dimensional image. Since the fluorescence response can be visualized two-dimensionally by using fluorescent imaging means, it becomes possible to view the target cells that express dipeptidyl peptidase IV instantaneously. Devices known in the art can be used as the fluorescent imaging device. Furthermore, in some cases the reaction of the dipeptidyl peptidase IV and the fluorescent probe can also be detected by the change in the ultraviolet-visible absorption spectrum (for example, a change in absorbance at a specific absorption wavelength).

Typical examples of the means of bringing the sample to be measured and the fluorescent probe into contact include adding, applying, or spraying a solution comprising the fluorescent probe on a sample, nonetheless, a suitable means can be selected in accordance with the form of the sample, the measurement environment, or the like. When a solution comprising the fluorescent probe Is sprayed on a sample, a device equipped, for example, with a chemical solution housing unit for housing the chemical solution comprising the fluorescent probe and a chemical solution spray unit constructed to permit the chemical solution to be sprayed onto the sample to be measured, can be used. Such a device may be an endoscope. Examples of endoscopes having such a function are disclosed, for example, in JP Kokai 2010-240188 and JP Kokai 2015-23304. In addition, the device can also be equipped with fluorescent imaging means as described above for observing the fluorescence response due to the fluorescent probe.

The applicable concentration of the fluorescent probe of the present invention is not particularly restricted; for example, a solution of a concentration of about 0.1-10 µM can be applied.

Detection of dipeptidyl peptidase IV by the method of the present invention can generally be conducted under neutral conditions, for example a range of pH 5.0-9.0, preferably a range of pH 6.0-8.0, more preferably a range of pH 6.8-7.6. Any pH adjusters and buffers known in the art such as phosphate buffer and the like can be used as the means for adjusting the pH.

5. Kit

A kit for detecting dipeptidyl peptidase IV (DPP-IV) comprising the above fluorescent probe is preferably used in the detection method of the present invention. In particular, when the above protease is chymotrypsin, the kit preferably includes the above fluorescent probe and trypsin, and the fluorescent probe and trypsin are preferably stored so that they do not mix during the time prior to conducting measurement. The fluorescent probe of the present invention is usually prepared as a solution in this kit, but it can also be provided as a composition of a suitable form such as a mixture in powdered form, freeze-dried product, granules, tablets, liquid, or the like, and can also be applied dissolved in distilled water for injection or a suitable buffer at the time of use.

This kit may also include other reagents and the like as needed. For example, dissolution auxiliaries, pH adjusters, buffers, isotonifying agents, and other such additives can be used as additives, and the amounts compounded can be selected as appropriate by one skilled in the art.

EXAMPLES

The present invention is explained in greater detail, below through examples, but the invention is not limited to these examples.

Example 1

1. Synthesis of a Fluorescent Probe

Hydroxymethyl rhodamine green (HRMG) having various dipeptide sites was synthesized in accordance with the following scheme. Furthermore, compounds 1-6 having different dipeptide sites were obtained by varying the Fmoc-amino acid used during the synthesis of compound A7.

[Chemical formula 6]
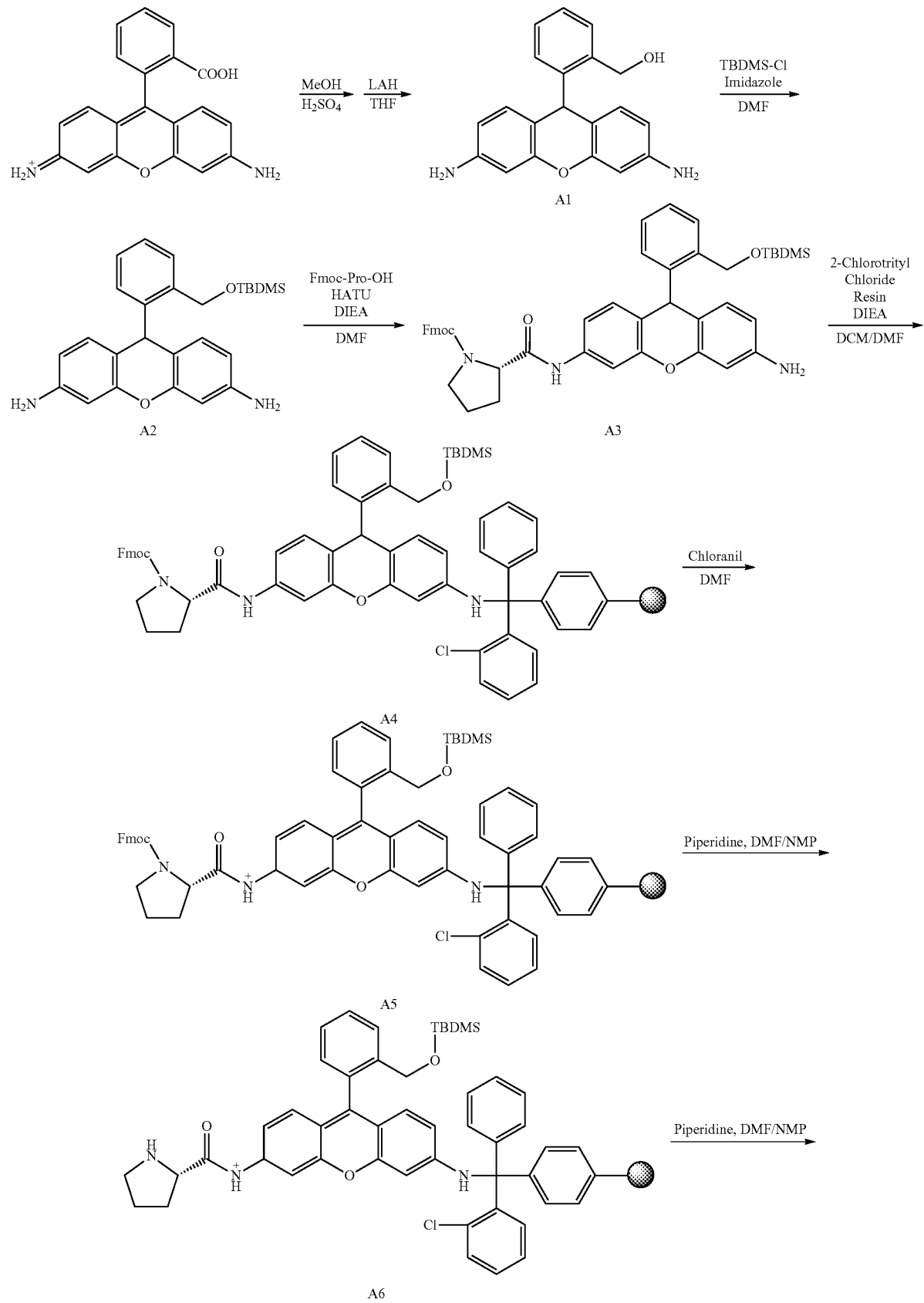

-continued

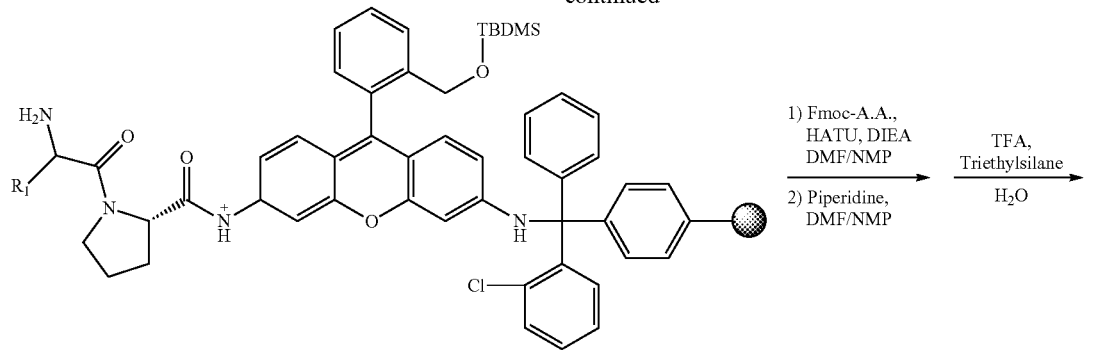

A7

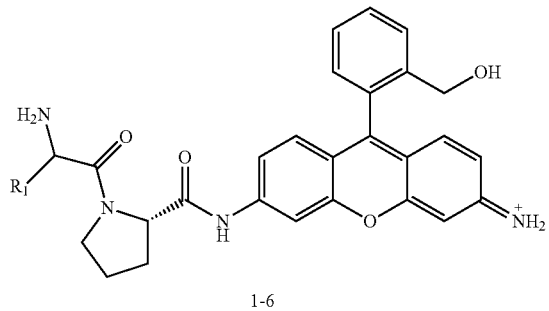

1-6

Synthesis of Compound A1

One thousand one hundred twenty-seven milligrams (3.12 mmol, 1 Eq) of rhodamine 110 chloride was dissolved in 180 mL of methanol and stirred overnight at 80° C. in an argon atmosphere after adding 9 mL of sulfuric acid. After cooling to room temperature, the reaction solvent was removed under reduced pressure, the residue was neutralized by adding saturated sodium bicarbonate aqueous solution, and the solution was filtered. The solid obtained by filtration was dissolved in methanol and recovered, and the methanol was removed under reduced pressure. The residue was dissolved in 200 mL of tetrahydrofuran, 1545 mg (40.7 mmol, 13 Eq) of lithium aluminum hydride was added while stirring in an ice bath, and the solution was stirred overnight at room temperature in an argon atmosphere, shielded from light by aluminum foil. After adding 30 mL of methanol while stirring the reaction solution in an ice bath, the reaction solvent was removed under reduced pressure. Two hundred milliliters of saturated Rochelle salt aqueous solution and 100 mL of ethyl acetate were added to the residue, and stirred overnight in an argon atmosphere, shielded from light by aluminum foil. After extracting the ethyl acetate layer from the reaction solution by a separation procedure, the ethyl acetate was removed under reduced pressure. The residue was purified by silica gel chromatography (dichloromethane/msthanol=90/10), and the target compound (557 mg, 56%) was obtained.

$^1$H NMR (300 MHz, CD$_3$OD): δ4.63 (s, 2H), 5.38 (s, 1H), 6.30 (dd, 2H, J=2.1, 9.0 Hz), 6.41 (d, 2H, J=2.1 Hz), 6.64 (d, 2H, J=9.0 Hz), 7.04-7.08 (m, 1H), 7.14-7.16 (m, 2H), 7.39-7.42 (m, 1H)

$^{13}$C NMR (100 MHz, CD$_3$OD): δ40.2, 63.0, 103.4, 112.2, 115.4, 127.3, 128.7, 128.9, 131.2, 131.9, 145.7, 148.5, 152.8
HRMS (ESI$^+$): calcd for [M+H]$^+$, 319.14018 found, 319.14465 (−4.48 mmu).

Synthesis of Compound A2

Five hundred fifty-seven milligrams (1.75 mmol, 1 Eq) of compound A1, 402 mg (2.66 mmol, 1.5 Eq) of t-butyldimethylsilyl chloride, and 242 mg (3.55 mmol, 2 Eq) of imidazole were dissolved in 25 ml, of N,N'-dimethylformamide and stirred for four hours in an argon atmosphere, shielded from light by aluminum foil. After adding 100 mL of water, ethyl acetate was added, and the ethyl acetate layer was extracted by a separation procedure. The ethyl acetate was removed under reduced pressure, and the residue was purified by silica gel column chromatography (ethyl acetate/hexane=2/3), and the target compound (713 mg, 94%) was obtained, $^1$H NMR (400 MHz, aceton-d$_6$): δ0.11 (s, 6H), 0.98 (s, 9H), 4.72 (s, 4H), 4.79 (s, 2H), 5.44 (s, 1H), 6.35 (dd, 2H, J=2.9, 10.7 Hz), 6.46 (d, 2H, J=2.9 Hz), 6.71 (d, 2H, J=10.7 Hz), 7.22-7.29 (m, 3H), 7.53-7.57 (m, 1H)

$^{13}$C NMR (75 MHz, CDCl$_3$): δ−5.47, 18.3, 25.9, 39.1, 62.9, 102.0, 110.6, 114.1, 126.4, 127.2, 127.4, 130.4, 130.7, 138.5, 143.9, 146.0, 151.3
HRMS (ESI$^+$): calcd for [M+H]$^+$, 433.23113 found, 433.23114 (0.0 mmu).

Synthesis of compound A3

Three hundred eleven milligrams (0.720 mg, 2 Eq) of compound A2, 124 mg (0.368 mmol, 1 Eq) of Fmoc-proline, and 137 mg (0.360 mmol, 1 Eq) of HATU were dissolved in 5 mL of N,N'-dimethylformamide, followed by addition of 128 μL (0.722 mmol, 2 Eq) of N,N-diisopropylethylamine and stirring for 90 minutes at 50° C. in an argon atmosphere. After removing the reaction solvent under reduced pressure, the residue was dissolved in ethyl acetate, saturated saline was added, and a separation procedure was performed. The ethyl acetate layer was extracted and removed under reduced pressure, and the residue obtained was purified by silica gel column chromatography (ethyl acetate/hexane=1/1), and the target compound (167 mg, 62%) was obtained.

HRMS (ESI$^+$): calcd for [M+H]$^+$, 752.35197; found, 752.35316 (1.19 mmu).

Synthesis of Compound A4

One hundred sixty-seven milligrams (0.222 mmol, 1.5 Eq) of compound A3 were dissolved in 1.6 mL of dichloromethane and 0.4 mL of N,N'-dimethylformamide, then 102 mg (0.145 mmol, 1 Eq) of 2-chlorotrityl chloride resin and 200 μL (1.13 mmol, 7.8 Eq) of N,N-diethylisopropylamine were added and stirred for 24 hours in an argon atmosphere, shielded from light by aluminum foil. After removing the reaction solvent by filtration, the resin was washed by dichloromethane/methanol/N,N-diisopropylethylamine-17/2/1 mixed solution and dichloromethane. The resin obtained was divided into six equal parts.

Compounds A5-A7 and compounds 1-6 were synthesized below in accordance with a peptide solid-phase synthesis method.

Synthesis of Compound A5

The A4 obtained was divided into six equal parts, and 1.1 mL of N,N-dimethylformamide was added to each. After shaking for one hour, the solution was removed by filtration, and 1.6 mL of tetrachloro-p-bensoquinone 120 mM N,N'-dimethylformamide solution was added and shaken for 30 minutes. The solution was removed by filtration, 1.1 mL of N,N'-dimethylformamide was added and shaken for one minute, and the solution was removed by filtration.

Synthesis of Compound A6

A quantity of 800 μL of 20% piperidine/N,N'-dimethylformamide solution (v/v) was added and shaken for three minutes, the solution was removed by filtration, 800 μL of 20% piperidine/N,N'-dimethylformamide solution (v/v) was again added and shaken for 12 minutes, and the solution was removed by filtration. The operation of adding 900 μL of N,N'-dimethylformamide and shaking for one minute, and removing the solution was conducted six times.

Synthesis of Compound A7

A quantity of 440 μL of 440 mM HATU/N,N'-dimethylformamide solution, 200 μL of 2 M N,N'-diethylisopropylamine/N-methylpyrrolidone solution, and 400 μL of 480 mM Fmoc-amino acid (1; Fmoc-glycine, 2; Fmoc-t-butyl-glutamic acid, 3; Fmoc-Boc-lysine, 4; Fmoc-t-butyl-tyrosine, 5; Fmoc-leucine, 6; Fmoc-proline)/N,N'-dimethylformamide solution were shaken for two hours. The solution was removed by filtration, 900 μL of N,N'-dimethylformamide was added and shaken for one minute, and the solution was removed. A quantity of 440 μL of 440 mM HATU/N,N'-dimethylformamide, 200 μL of 2 M N,N-diethylisopropylamine/N-methylpyrrolidone solution, and 400 μL of 480 mM Fmoc-amino acid (the following were used respectively in accordance with compounds 1-6. 1; Fmoc-glycine, 2; Fmoc-t-butyl-glutamic acid, 3; Fmoc-Boc-lysine, 4; Fmoc-t-butyl-tyrosine, 5; Fmoc-leucine, 6; Fmoc-proline)/N,N'-dimethylformamide solution were again shaken for two hours. The solution was removed by filtration, 900 μL of N,N'-dimethylformamide was added and shaken for one minute, and the solution was removed. A quantity of 440 μL of 440 mM HATU/N,N'-dimethylformamide, 200 μL, of 2 M N,N'-diethylisopropylamine/N-methylpyrrolidone solution, and 400 μL of 480 mM Fmoc-amino acid (1; Fmoc-glycine, 2; Fmoc-t-butyl-glutamic acid, 3; Fmoc-Boc-lysine, 4; Fmoc-t-butyl-tyrosine, 5; Fmoc-leucine, 6; Fmoc-proline)/N,N'-dimethylformamide solution were shaken a third time for one hour. The solution was removed by filtration, 900 μL of N,N'-dimethylformamide was added and shaken for one minute, and the solution was removed. A quantity of 800 μL of 20% piperidine/N,N'-dimethylformamide solution (v/v) was added and shaken for three minutes, the solution was removed by filtration, 800 μL of 20% piperidine/N,N'-dimethylformamide solution (v/v) was again added and shaken for 12 minutes, and the solution was removed by filtration. The operation of adding 900 μL of N,N'-dimethylformamide and shaking for one minute, and removing the solution was conducted six times.

Synthesis of Compound A7

The resin obtained was transferred to a 30 mL vial, and 2 mL of trifluoroacetic acid, 200 μL of water, and 200 μL of triethylsilane were added and stirred for two hours. The resin was removed by filtration. After washing with acetonitrile, the filtrate was distilled under reduced pressure, and 40 mL of diethyl ether was added to the residue and centrifuged for 10 minutes at 3000 rpm. The diethyl ether was removed, 40 mL of diethyl ether was again added and centrifuged for 10 minutes at 3000 rpm, and the diethyl ether was removed. After air drying the residue overnight, it was purified using HPLC. Compound 1-4, 6 was purified by HPLC (eluent A ($H_2O$ 0.1% TFA) and eluent B ($CH_3CN$ 80%, $H_2O$ 20%, 0.1% TFA) (A/B=80/20 to 25/75, 45 min)), and the target compound was obtained. Compound 5 was purified by HPLC (eluent A ($H_2O$ 0.1% TFA) and eluent B ($CH_3CN$ 80%, $H_2O$ 20%, 0.1% TFA) (A/B=80/20 to 25/75, 45 min)), further purified by HPLC (eluent A ($H_2O$ 0.1% TFA) and eluent B ($CH_3CN$ 80%, $H_2O$ 20%, 0.1% TFA) (A/B=80/20 to 25/75, 45 min)), finally purified by HPLC (eluent A ($H_2O$ 0.1% TFA) and eluent B ($CH_3CN$ 80%, $H_2O$ 20%, 0.1% TFA) (A/B=80/20 to 25/75, 45 min)), and the target compound was obtained.

[Yields] Compound 1; 4.7 mg, 42%, compound 2; 3.2 mg, 25%, compound 3; 5.1 mg, 39%, compound 4; 3.2 mg, 23%, compound 5; 4.3 mg, 34%, compound 6; 6.7 mg, 55%)

Example 2

2. DPP-IV Assay by Fluorescent Probe

The absorption spectra and fluorescence spectra of compound 1 (GP-HRMG) having a glycine-proline dipeptide site synthesized in Example 1 and hydroxymethyl rhodamine green (HRMG) not having a dipeptide site were each measured. The results are shown in Table 1.

TABLE 1

| | Maximum absorption wavelength (nm) | Maximum fluorescence wavelength (nm) | Molar extinction coefficient $M^{-1}cm^{-1}$ at pH 7.4 | Fluorescence quantum yield | pKcycl |
|---|---|---|---|---|---|
| HMRG | 501 | 524 | 57,000 | 0.81 | 8.1 |
| GP-HMRG | 496 | 527 | 300 | — | 5.0 |

The results in Table 1 showed that compound 1, which is a fluorescent probe of the present invention, is present mainly in a colorless, non-fluorescent, closed-ring structure under neutral conditions.

Next, DPP-IV was caused to act on compound 1, and the changes in the absorption spectrum and fluorescence spectrum were measured. The results are shown in FIG. 1 (the concentration of compound 1 was 3.5 μM). An increase in the absorbance and fluorescence intensity of compound 1 were obtained in association with addition of DPP-IV based on FIG. 1.

Figure 2:
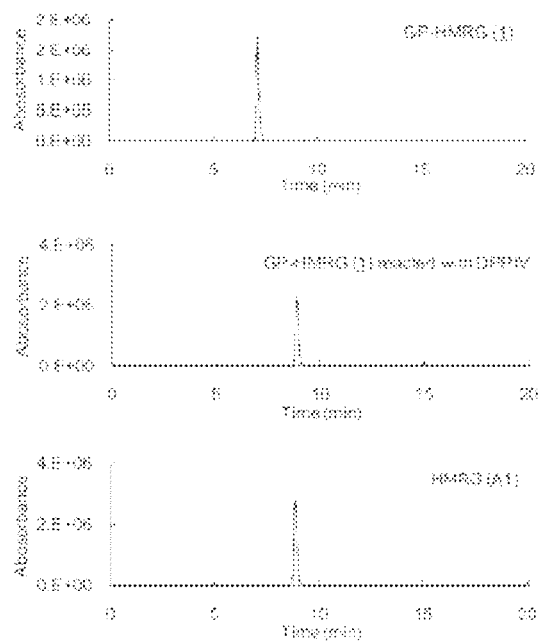
FIG. 2 Shows an HPLC chromatogram associated with addition of DPP-IV to GP-HRMG, which is a fluorescent probe of the present invention.

Similarly, DPP-IV was caused to act on compound 1, and analysis was conducted by HPLC chromatography. The results obtained are shown in FIG. 2. FIG. 2 shows that since the peak position of compound 1 becomes the same as that of HRMG due to reaction with DPP-IV, the dipeptide site of compound 1 is hydrolyzed and cleaved by DPP-IV.

Figure 3:
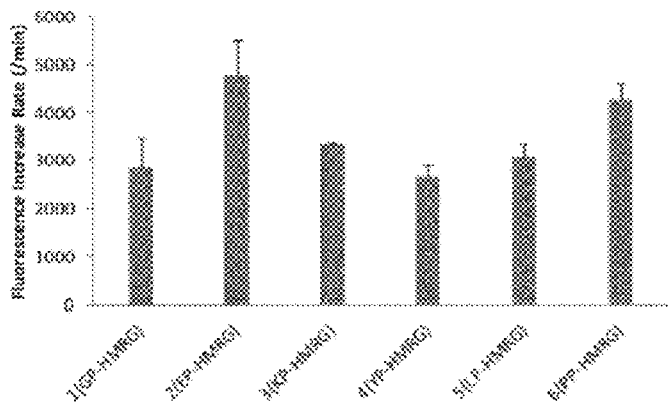
FIG. 3 Graph showing the fluorescence intensity increase rate of a fluorescent probe of the present invention six minutes after addition of DPP-IV.
Figure 4:
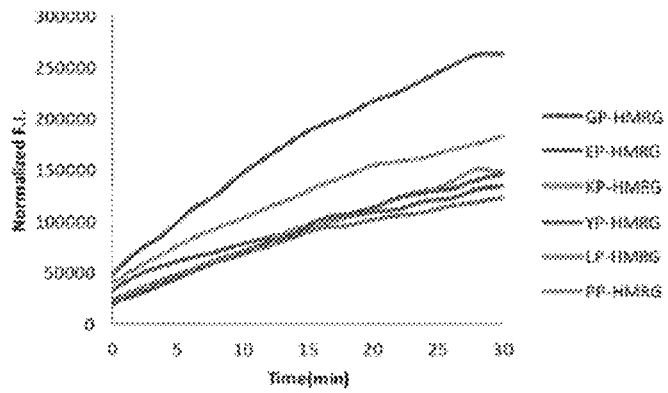
FIG. 4 Graph that plots the time dependence ox the fluorescence intensity of a fluorescent probe of the present invention associated with DPP-IV addition.

In addition to compound 1, fluorescence assays were conducted on compounds 2-6 synthesized in the same way in Example 1. For the solution conditions, a solution comprising 18 μL of solution comprising a fluorescent probe concentration of 1.1 μM and 20 mM Tris HCl buffer (pH 7.1), and 2 μL of solution comprising DPP-IV and 20 mM Tris HCl buffer was used. The results obtained by adding DPP-IV to each solution containing a fluorescent probe and measuring the increase in the fluorescence intensity are shown in FIGS. 3 and 4 (excitation wavelength 501 nm, fluorescence wavelength 524 nm). FIG. 3 is a graph snowing the fluorescence intensity increase rate six minutes after DPP-IV addition; FIG. 4 is a graph plotting the time dependence of the fluorescence intensity. These results clarified that all of the compounds function as fluorescent probes for DPP-IV and that the fluorescence intensify increase rate depends on the type of dipeptide site.

Example 3

3. Live Cell Imaging in Cultured Esophageal Cancer Cells

Imaging was conducted over time after adding GP-HMRG (compound 1) to six types of human esophageal squamous cell carcinoma cells.

As human esophageal squamous cell carcinoma cells, two highly differentiated types (KYSE30, KYSE270), two moderately differentiated types (KYSE140, KYSE520), and two lowly differentiated types (KYSE150, KYSE 1170) were cultured for two days at 37° C., 5% $CO_2$ using a μ-Slide 8 well. After adding 0.2 μL of a DMSO solution (10 mM) of GP-HMRG (compound 1) dissolved in 200 μL of RPMI 1640 (phenol red-free) (final probe concentration 10 μM) dropwise thereto, the cells were observed for 60 minutes using a TCS SP5. As an inhibitor experiment, the cells were observed for 60 minutes using a TCS SP5 in the same way after dropwise addition of 5 μM of GP-HMRG (compound 1) and 100 μM of DPP-IV inhibitor dissolved in 200 μL of RPMI 1640 (phenol red-free).

Figure 5:
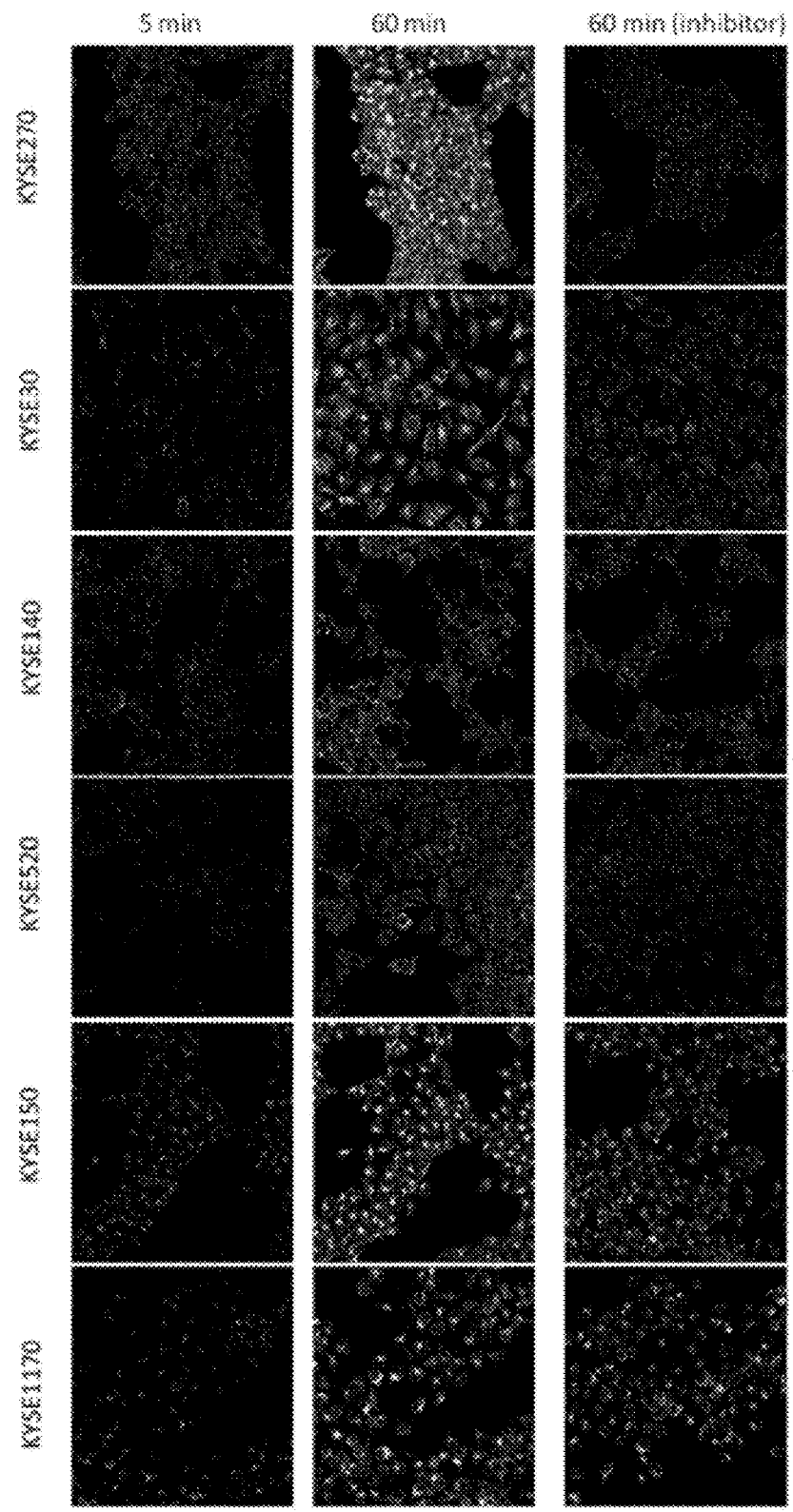
FIG. 5 Live cell imaging image in cultured esophageal cancer cells using a fluorescent probe of the present invention.

As a result, an increase in fluorescence intensity was seen over time in all of the cells. In addition, the fluorescence intensity was lower with the probe with inhibitor added than with probes with no inhibitor added (FIG. 5).

Example 4

4. Imaging of Human Esophageal Cancer Biopsy Specimens

One biopsy sample each from a tumor area and non-tumor area were collected from patients undergoing preoperative upper endoscopy, and imaging and fluorescence intensity were measured over time after dropwise addition of various fluorescent probes (compounds 1-6).

Figure 6:
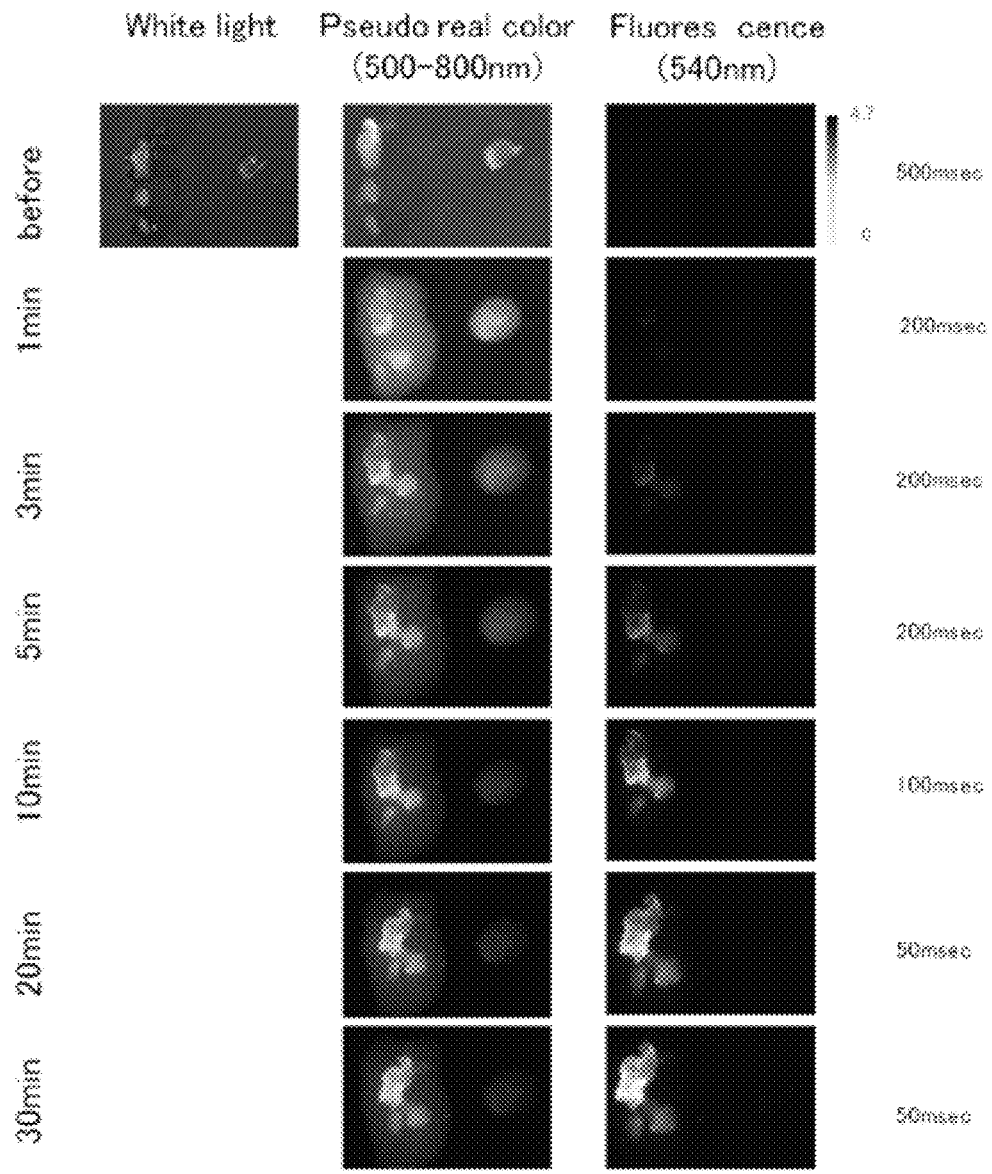
FIG. 6 Imaging image of human esophageal cancer biopsy specimens using a fluorescent probe of the present invention.
Figure 7:
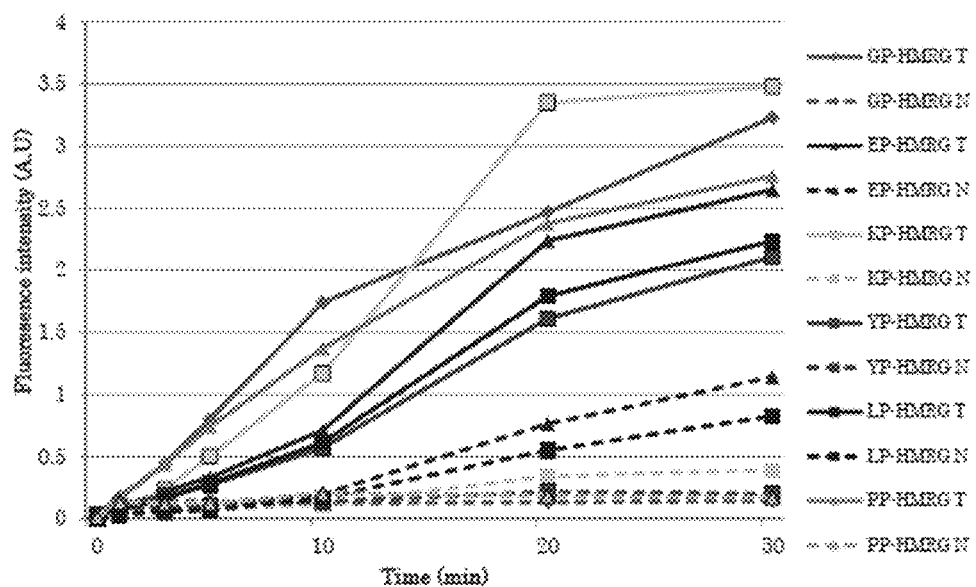
FIG. 7 Graph that plots the time dependence of the fluorescence intensity in the imaging of FIG. 6.

0.5 μL of a DMSO solution (10 mM) of the various fluorescent probes was dissolved in 100 μL of RPMI 1640 (phenol red-free) (final probe concentration 50 μM), and 50 μL of the resulting solution was added dropwise to each of the specimens, whereupon the fluorescence intensity was measured over 30 minutes using a Maestro In Vivo Imaging System Ex. As a result, the fluorescence intensity was found to have increased in the tumor areas in comparison to the non-tumor areas (FIGS. 6 and 7). Furthermore, immunostaining showed high expression of DPP-IV in tissues of the tumor areas.

In addition, since it was possible to gather ten or more cases for GP-HMRG (compound 1), EP-HMRG (compound 2), and PP-HMRG (compound 6), the cut-off value was calculated from the data using an ROC curve, and the sensitivity, specificity, correct diagnosis rate, positive predictive value, and negative predictive value were determined. The results were not inferior to the conventional methods NBI (narrow band imaging) and iodine staining (Table 2(a)-(c)).

TABLE 2

| | 5 min | 10 min | 30 min |
|---|---|---|---|
| (a) GP-HMRG (compound 1) | | | |
| (tumor area: 14 cases, non-tumor area: 17 cases) | | | |
| AUC | 0.99 | 0.98 | 0.95 |
| Cut-off | 0.54 | 1.02 | 2.10 |
| Sensitivity | 100 | 100 | 92.9 |
| Specificity | 94.1 | 94.1 | 88.2 |
| Correct diagnosis rate | 96.8 | 96.8 | 90.3 |
| Positive predictive value | 93.3 | 93.3 | 86.7 |
| Negative predictive value | 100 | 100 | 93.8 |
| (b) EP-HMRG (compound 2) | | | |
| (tumor areas: 32 cases, non-tumor areas: 42 cases) | | | |
| AUC | 0.93 | 0.93 | 0.95 |
| Cut-off | 0.37 | 0.67 | 1.77 |
| Sensitivity | 96.9 | 96.9 | 96.9 |
| Specificity | 85.4 | 83.3 | 90.5 |
| Correct diagnosis rate | 90.5 | 89.2 | 93.2 |
| Positive predictive value | 83.8 | 81.6 | 88.6 |
| Negative predictive value | 97.3 | 97.2 | 97.4 |
| (c) PP-HMRG (compound 3) | | | |
| (tumor areas: 15 cases, non-tumor areas: 13 cases) | | | |
| AUC | 0.88 | 0.94 | 0.94 |
| Cut-off | 0.54 | 0.64 | 1.44 |
| Sensitivity | 66.7 | 93.3 | 92.9 |
| Specificity | 100 | 84.6 | 83.3 |
| Correct diagnosis rate | 82.1 | 89.3 | 88.5 |
| Positive predictive value | 100 | 87.5 | 86.7 |
| Negative predictive value | 72.2 | 91.7 | 90.9 |

Example 5

5. Imaging of Human Esophageal Surgical Specimens and ESD Specimens

Esophageal specimens from patients who underwent surgery and endoscopic submucosal dissection (ESD) for esophageal cancer were brought immediately after removal in each treatment (meaning surgical specimens and ESD specimens, respectively) to an imaging room, and imaging was conducted over time after spraying the specimens directly with various fluorescent probes (compounds 1-6). For surgical specimens, 10 μL of a DMSO solution (10 mM) of the various fluorescent probes was dissolved in 2 mL of RPMI 1640 (phenol red-free) (final probe concentration 50 μM), and imaging was conducted using a Maestro In Vivo Imaging System Ex after spraying the fluorescent probe on the specimen using a spray tube for an endoscope. For ESD specimens, 3 μL of a DMSO solution (10 mM) of the various fluorescent probes was dissolved in 600 μL of RPMI 1640 (phenol red-free) (final probe concentration 50 μM), and imaging was conducted using a Maestro In Vivo Imaging System Ex after adding the fluorescent probe dropwise to the specimen.

Figure 8A:
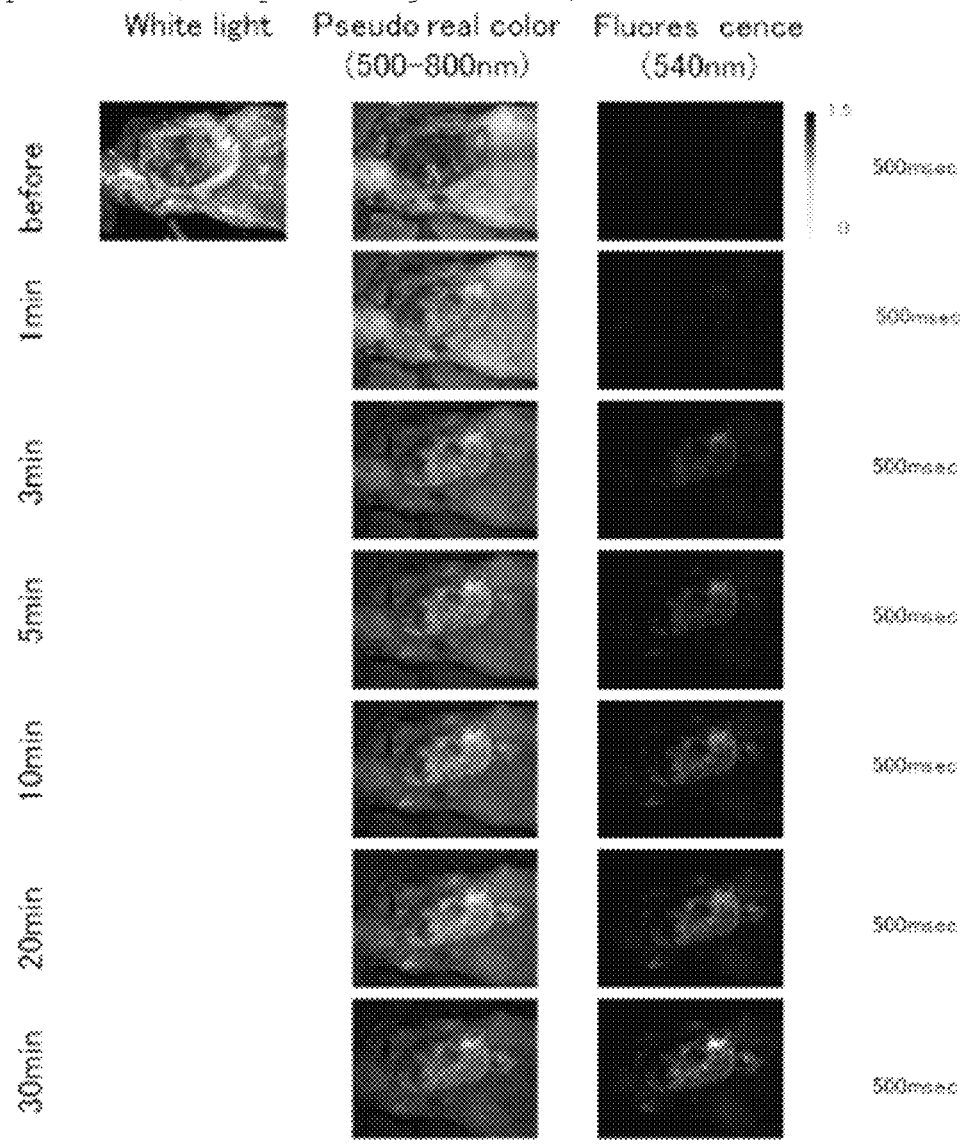
FIG. 8 Imaging image (FIG. 8a) of human esophageal cancer surgical specimens using a fluorescent probe of the present invention, and an image showing a comparison with an iodine stained image (FIG. 8b).
Figure 8A:
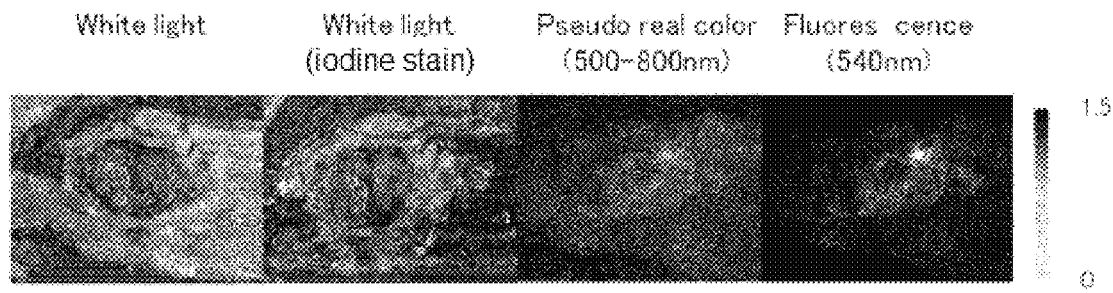
Figure 9A:
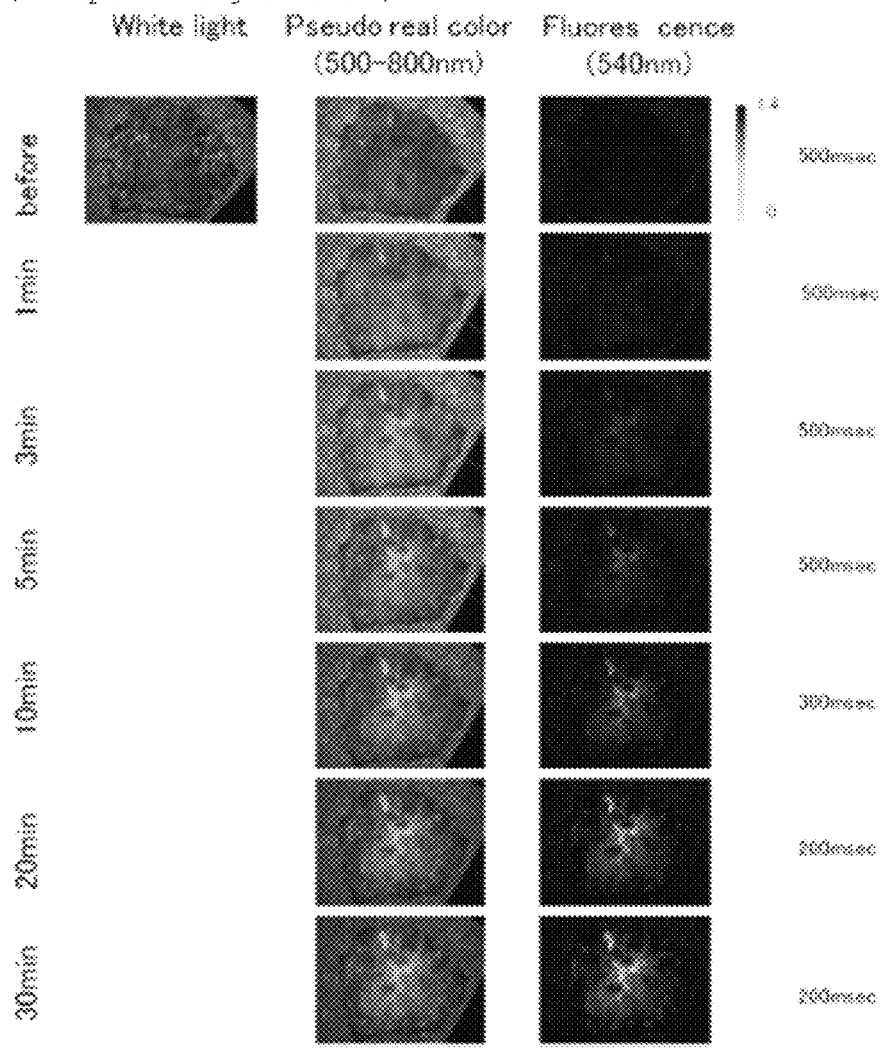
FIG. 9 Imaging image (FIG. 9a) of human esophageal cancer ESD specimens using a fluorescent probe of the present invention, and an image showing a comparison with an iodine stained image (FIG. 9b).
Figure 9A:
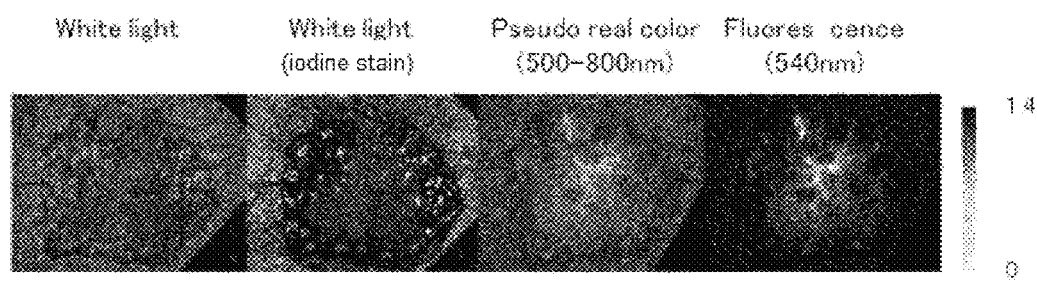

As a result, visualization of the tumor area was achieved several minutes after spraying the probe (FIGS. 8 and 9). DPP-IV expression was observed by immunostaining in specimens imaged by the fluorescent probes, and was observed to correspond to the above fluorescent imaging results.

Figure 10:
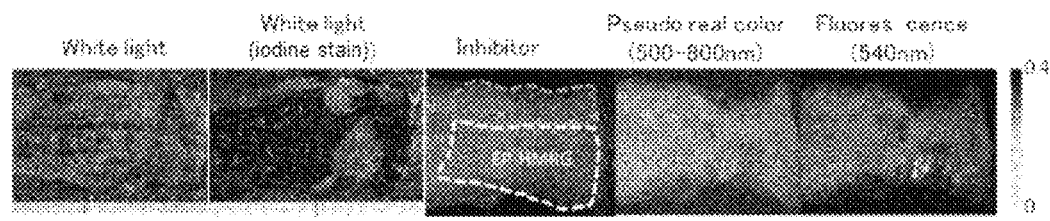
FIG. 10 Imaging image of human esophageal cancer surgical specimens when inhibitor was added.

In addition, an inhibitor experiment was conducted using surgical specimens to show that the fluorescent probe reacts to DPP-IV. Specifically, gauze impregnated with 5 μL of a DMSO solution (10 mM) of EP-HMRG (compound 2)

dissolved in 1 mL of RPMI 1640 (phenol red-free) (final probe concentration 50 μM) and gauze impregnated with 5 μL of a DMSO solution (10 mM) of EP-HMRG (compound 2) and 5 μL of a DPP-IV inhibitor (10 mM) dissolved in 1 mL of RPMI 1640 (phenol red-free) were used. Each was adhered for five minutes so as to cover half the specimen, and imaging was conducted thereafter. As a result, an increase in fluorescence intensity was not seen in tumor areas at sites were a probe comprising inhibitor had been sprayed (FIG. 10).

The above results prove that the presence of human esophageal cancer can be detected at high sensitivity by using a fluorescent probe of the present invention.

The invention claimed is:

1. A fluorescent probe for detecting dipeptidyl peptidase IV (DPP-IV), the fluorescent probe comprising a compound represented by the following formula (I) or a salt thereof:

[Chemical formula I]

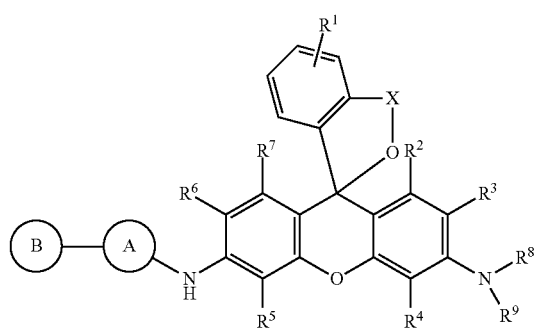

wherein A and B are either the same or different and independently represent amino acid residues; wherein A is bonded via an amide bond to the adjacent NH in formula (I) and B is bonded via an amide bond to A; $R^1$ represents hydrogen atom or one to four of the same or different substituents bonded to a benzene ring; $R^2$, $R^3$, $R^4$, $R^5$, $R^6$, and $R^7$ each independently represent a hydrogen atom, hydroxyl group, alkyl group, or halogen atom; $R^8$ and $R^9$ each independently represent a hydrogen atom or alkyl group; X represents a $C_1$-$C_3$ alkylene group.

2. The fluorescent probe according to claim 1 wherein A is an amino acid residue selected from proline or alanine.

3. The fluorescent probe according to claim 2 wherein B is an amino acid residue selected from glycine, glutamic acid, lysine, tyrosine, leucine, or proline.

4. The fluorescent probe according to claim 3 wherein A is a proline residue and B is a glycine residue.

5. The fluorescent probe according to any of claims 1-4 wherein $R^1$, $R^2$, $R^3$, $R^4$, $R^5$, $R^6$, $R^7$, $R^8$, and $R^9$ are hydrogen atoms, and X is a methylene group.

6. A fluorescent probe according to claim 1 for detecting dipeptidyl peptidase IV (DPP-IV) comprising a compound selected from the following group, or a salt thereof:

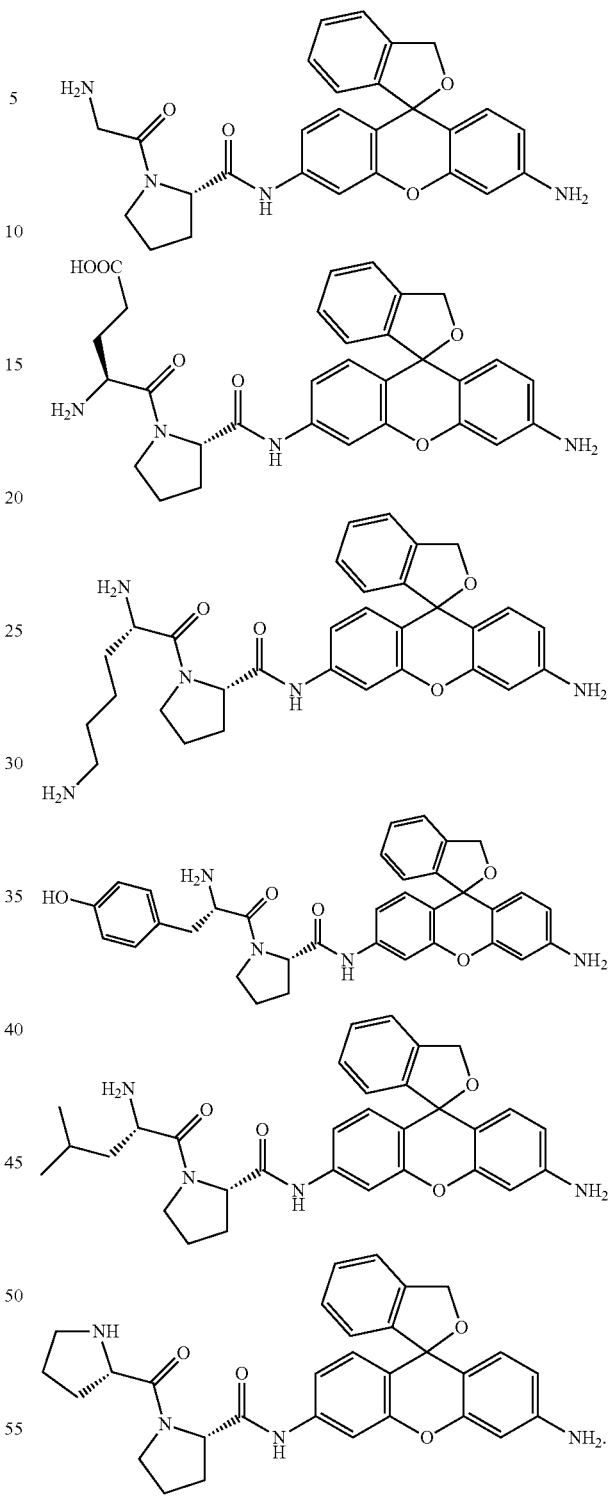

7. A method for detecting dipeptidyl peptidase IV comprising:

bringing the fluorescent probe according to claim 1 into contact with a sample, observing a fluorescence response due to a reaction of the dipeptidyl peptidase IV (DPP-IV) in the sample and the fluorescent probe.

8. The method according to claim 7, wherein the observing step comprises visualizing the fluorescence response using fluorescent imaging means.

9. A method for detecting target cells that express dipeptidyl peptidase IV (DPP-IV) comprising: bringing the fluorescent probe according to claim 1 into contact with the target cells, observing a fluorescence response due to a reaction of the dipeptidyl peptidase IV (DPP-IV) in the target cells and the fluorescent probe.

10. The method according to claim 9 wherein the target cells are cancer cells.

11. The method according to claim 10 wherein the cancer cells are esophageal cancer cells.

12. A kit for detecting dipeptidyl peptidase IV (DPP-IV) comprising the fluorescent probe according to 1.

* * * * *